United States Patent [19]

Schuster et al.

[11] 4,171,459
[45] Oct. 16, 1979

[54] MANUFACTURE OF α-NAPHTHOL

[75] Inventors: Ludwig Schuster, Limburgerhof; Bernhard Seid, Frankenthal, both of Fed. Rep. of Germany

[73] Assignee: BASF Aktiengesellschaft, Fed. Rep. of Germany

[21] Appl. No.: 876,758

[22] Filed: Feb. 10, 1978

[30] Foreign Application Priority Data

Feb. 17, 1977 [DE] Fed. Rep. of Germany ....... 2706682

[51] Int. Cl.$^2$ ............................................. C07C 39/08
[52] U.S. Cl. .................................................. 568/735
[58] Field of Search ........................ 568/735, 740, 877

[56] References Cited
U.S. PATENT DOCUMENTS 2,511,467  6/1950  Gresham ............................. 568/877
2,639,298  5/1953  Head .................................... 568/755
3,239,572  3/1966  Zinstag ................................. 568/877
3,317,593  5/1967  Enk et al. ............................. 568/877

FOREIGN PATENT DOCUMENTS 326762  3/1930  United Kingdom ..................... 568/735

*Primary Examiner*—Werren B. Lone
*Attorney, Agent, or Firm*—Keil & Witherspoon

[57] ABSTRACT

Process for the manufacture of α-naphthol by hydrolyzing α-naphthyl esters of aliphatic carboxylic acids in a distillation column by means of steam in counter-current at a particular temperature, and in a certain ratio, in the presence of organic sulfonic acids. The α-naphthol obtainable by the process of the invention is a valuable starting material for the manufacture of dyes, drugs and insecticides, e.g. α-naphthyl N-methylcarbamate.

11 Claims, No Drawings

MANUFACTURE OF α-NAPHTHOL

The present invention relates to a new process for the manufacture of α-naphthol by hydrolyzing α-napthyl esters of aliphatic carboxylic acids in a distillation column by means of steam in counter-current at a particular temperature, and in a certain ratio, in the presence of organic sulfonic acids.

Ullmanns Encyklopädie der technischen Chemie, volume 18, pages 72 and 73 discloses that esters can be hydrolyzed catalytically to the alcohol and the acid by means of water in the presence of an acid or base. In the case of esters of alkanecarboxylic acids, e.g. of fatty acids, the hydrolysis to the acid is a rule carried out under pressure in the presence of emulsifiers. Optimal hydrolysis is achieved by heating the ester for five hours in a mixture of formic acid and methanesulfonic acid.

As shown by the Comparative Example, the hydrolysis of α-naphthyl esters, especially α-naphthyl acetate, is a very slow reaction. To carry out the hydrolysis, the ester must be thoroughly mixed for several hours with water at 200° C. under a pressure of up to 20 bars. However, when carried out in this way the hydrolysis only proceeds to an equilibrium at which, when using economically acceptable amounts of water, there are still about 2 percent by weight of ester present. Under the severe reaction conditions employed, substantial corrosion of the materials of the vessels occurs, so that expensive, highly resistant materials of construction, e.g. titanium or tantalum, must be used. The reaction gives a dilute acetic acid which, before it can be re-used, must be re-concentrated in an expensive process step.

German Published Patent Application No. B 64 09.12 0, 11 discloses running a mixture of water and carboxylic acid ester into the upper part of a distillation column, introducing steam into the column at a lower point, and heating the column so that the acid formed distils off. The reaction is carried out in the presence of hydrolysis catalysts; the catalysts named are mineral acids, e.g. sulfuric acid, silica gel and solid synthetic resin ion exchangers which are used for water purification, e.g. a phenol/formaldehyde/sodium sulfite condensation product. Only monohydric or polyhydric aliphatic alcohols are mentioned as the alcohol constituent of the ester. An essential feature of the process is that a large excess of water is used; a part of the water is introduced into the column as a mixture with the ester, and accordingly enters in co-current from above. Even this water, introduced in co-current with the ester, is advantageously used in excess over the latter. The column temperature is set to a value where some water distils off continuously. The product taken off at the bottom is also a mixture of water and end product. As is shown in Example 3, the distillate still contains unconverted ester, and must be re-fractioned.

We have found that α-naphthol is obtained in an advantageous manner by hydrolyzing carboxylic acid esters with steam in a distillation column in the presence of an acid, if an α-naphthyl ester of an aliphatic carboxylic acid, of the formula

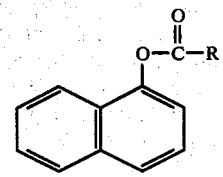

where R is hydrogen or an aliphatic radical, and an organic sulfonic acid is passed downward through the column whilst steam is passed upward in counter-current, and the reaction is carried out at from 100° to 170° C. using a ratio of from 0.9 to 1.5 moles of water per mole of α-naphthyl ester I.

Where α-naphthyl acetate is used, the reaction can be represented by the following equation:

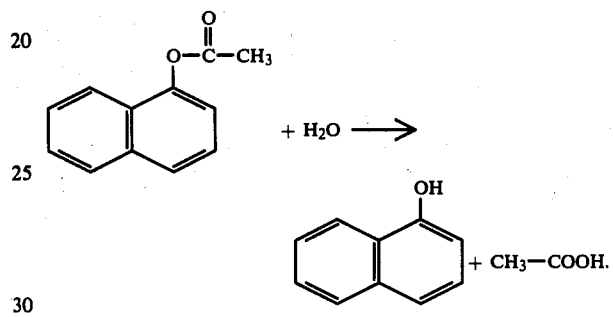

Compared to the prior art, the process of the invention gives α-naphthol more simply and more economically, and in better yield and greater purity. The process is also relatively more suitable for continuous operation and/or industrial operation. Compared to the German Patent Application cited above, the process of the invention gives a purer end product directly, with no substantial proportion of water or ester in the distillate or in the bottom product. No water is added to the starting material. Altogether, a substantial excess of water, relative to the ester, is not used; as a rule, virtually stoichiometric amounts are employed. The total amount of the water used is passed upward through the column, in counter-current. As a rule, the column is not heated. Neither the starting material nor the catalyst according to the invention are apparent from the cited German Patent Application.

Preferred starting materials I are those where R is hydrogen or alkyl of 1 to 7 carbon atoms, especially of 1 to 4 carbon atoms. The above radicals may be substituted by groups which are inert under the reaction conditions, e.g. alkyl or alkoxy each of 1 to 4 carbon atoms. Examples of suitable esters I are the α-naphthyl esters of formic acid, acetic acid, propionic acid, butyric acid, isobutyric acid, tetracosanoic acid, hexacosanoic acid, myristic acid, arachidic acid, behenic acid, caproic acid, enanthic acid, pelargonic acid, capric acid, 3,5,5-trimethylhexanoic acid, undecanoic acid, lauric acid, palmitic acid, stearic acid, 2-ethylhexanecarboxylic acid, α-ethylbutyric acid, 2-methylbutanoic acid, trimethylacetic acid, valeric acid, isovaleric acid, isocaproic acid, nonanoic acid, tridecanoic acid, pentadecanoic acid and heptadecanoic acid; formic acid, acetic acid and propionic acid are preferred.

The reaction is carried out at from 100° to 170° C., preferably from 120° to 155° C., especially from 130° to 145° C., under atmospheric or superatmospheric pressure, batchwise or, preferably, continuously. At lower temperatures, low-boiling constituents, e.g. acetic acid, are not substantially removed from the naphthol. For example, at temperatures near the boiling point of the carboxylic acid, the latter no longer distils off at the top of the column; it is true that the naphthyl acetate is hydrolyzed, but the second effect desired, i.e. the recovery of a concentrated carboxylic acid, e.g. acetic acid, is no longer achieved. On the other hand, at even higher temperatures a side-reaction of naphthol, namely the formation of condensed products of higher molecular weight under the action of the sulfonic acid, becomes more noticeable. The desired reaction temperature can within limits be controlled by the temperature of the individual reactants entering the column, e.g. steam and the naphthyl ester I. Additional heating or cooling can be effected through the walls of the column. Finally, in the case of substantial column diameters, trays comprising cooling coils or cooling pockets can be introduced. Preferably, the ester I is brought to from 120° to 180° C., preferably from 125° to 150° C., before entering the column.

The residence time is generally from 10 to 90, advantageously from 20 to 40, preferably from 20 to 36, minutes. The hydrolysis is carried out using a ratio of from 0.9 to 1.5, advantageously from 0.9 to 1.1, preferably from 0.95 to 1.05, moles of water, in the form of steam, per mole of α-naphthyl ester I. As a rule, virtually stoichiometric amounts of water and ester I are used. The steam may or may not be superheated and is advantageously supplied at from 100° to 170° C., preferably from 130° to 155° C., and at a pressure of from 1 to 3, preferably from 1 to 2, bars.

The organic sulfonic acids used may be aliphatic or aromatic. In general, the amount used is from 0.002 to 0.02, preferably from 0.005 to 0.01, mole of sulfonic acid per mole of starting material I. Advantageous sulfonic acids are monoalkanesulfonic acids of 1 to 6 carbon atoms, especially methanesulfonic acid, ethanesulfonic acid, propane-1-sulfonic acid, n-butane-1-sulfonic acid, n-pentane-1-sulfonic acid and n-hexane-1-sulfonic acid; alkanedisulfonic acids of 1 to 6 carbon atoms, especially methanedisulfonic acid and ethane-1,2-disulfonic acid; haloalkanesulfonic acids and hydroxyalkanesulfonic acids of 1 to 6 carbon atoms, especially 2-chloroethane-1-sulfonic acid, 2-hydroxyethane-1-sulfonic acid, 3-hydroxypropane-1- sulfonic acid, 3-hydroxybutane-1-sulfonic acid, 4-hydroxybutane-1-sulfonic acid, 1-chlorobutane-3-sulfonic acid and 1-chlorobutane-4-sulfonic acid; perfluorinated alkanesulfonic acids of 1 to 6 carbon atoms, especially perfluoromethanesulfonic acid, perfluoroethanesulfonic acid, perfluoropropane-1-sulfonic acid, perfluorobutane-1-sulfonic acid, perfluoropentane-1-sulfonic acid, and perfluorohexane-1-sulfonic acid; benzenesulfonic acids, especially benzenemonosulfonic acid, benzene-1,2-disulfonic acid, benzene-1,3-disulfonic acid, benzene-1,4-disulfonic acid, 2-methylbenzenesulfonic acid, 3-methylbenzenesulfonic acid, 4-methylbenzenesulfonic acid, 2,4-dimethylbenzenesulfonic acid, 2,5-dimethylbenzenesulfonic acid, 2,4,5-trimethylbenzenesulfonic acid, 4-isopropylbenzenesulfonic acid, 4-n-octylbenzenesuflonic acid and 2-, 3- or 4-dodecylbenzenesulfonic acid; partially hydrogenated aromatic sulfonic acids, e.g. indan-5-sulfonic acid and tetralin-2-sulfonic acid; carboxybenzenesulfonic acids, halobenzenesulfonic acids and hydroxybenzenesulfonic acids, especially 2-carboxybenzenesulfonic acid, 3-carboxybenzenesulfonic acid, 4-carboxybenzenesulfonic acid, 3,5-dicarboxybenzenesulfonic acid, 3,4-dicarboxybenzenesulfonic acid, 2-chloro-5-carboxybenzenesulfonic acid, 3-chloro-4-carboxybenzenesulfonic acid, 4-chlorobenzenesulfonic acid, 3-chlorobenzenesulfonic acid, 2-chlorobenzenesulfonic acid, 2,5dichlorobenzenesulfonic acid, 3,4-dichlorobenzenesulfonic acid, 2,4,5-trichlorobenzenesulfonic acid, 2-hydroxybenzenesulfonic acid, 3-hydroxybenzenesulfonic acid, 4-hydroxybenzenesulfonic acid, 3-chloro-4-methylbenzenesulfonic acid, 5-chloro-2-methylbenzenesulfonic acid, 4-chloro-3-methylbenzenesulfonic acid, 3-chloro-4-hydroxybenzenesulfonic acid and 5-chloro-2-hydroxybenzenesulfonic acid; polynuclear aromatic sulfonic acids, especially benzophenone-4-sulfonic acid, diphenylmethane-4-sulfonic acid, diphenylsulfone-3-sulfonic acid, naphthalene-1-sulfonic acid, naphthalene-2-sulfonic acid, naphthalene-1-5-disulfonic acid, naphthalene-1,6-disulfonic acid, naphthalene-2,6disulfonic acid, naphthalene-2,7-disulfonic acid, naphthalene-1,3,6-trisulfonic acid, diphenylether-4-sulfonic acid, acenaphthene-3-sulfonic acid, acenaphthene-5-sulfonic acid, 2,3-dibutyl-naphthalene-1-sulfonic acid, 2,4-dibutyl-naphthalene-1-sulfonic acid, 2,5-dibutyl-naphthalene-1-sulfonic acid, 2,6dibutyl-naphthalene-1-sulfonic acid, 2,7-dibutyl-naphthalene-1-sulfonic acid, 2,8-dibutyl-naphthalene-1-sulfonic acid, 1,3-dibutyl-naphthalene-2-sulfonic acid, 1,4-dibutyl-naphthalene-2-sulfonic acid, 1,5-dibutyl-naphthalene-2-sulfonic acid, 1,6-dibutyl-naphthalene-2-sulfonic acid, 1,7-dibutyl-naphthalene-2-sulfonic acid, 1,8-dibutyl-naphthalene-2-sulfonic acid and homologous dimethyl, diethyl, di-n-propyl, diisopropyl, diisobutyl, di-sec.-butyl and di-tert.-butyl derivatives of naphthalene-1-sulfonic acid and naphthalene-2-sulfonic acid, and mixtures of such compounds; the use of p-toluenesulfonic acid, o-, p- and m-dodecylbenzenesulfonic acid, 4-n-octylbenzenesulfonic acid, naphthalene-1-sulfonic acid, naphthalene-2-sulfonic acid and any of the above dibutylnaphthalenesulfonic acids, by themselves or in the form of mixtures, is preferred.

The distillation may be carried out in any distillation column, advantageously in a rectifying column, e.g. a sieve tray column, Oldershaw column, thin layer evaporator, falling curtain distillation apparatus, glass tray column, bubble-cap tray column, valve tray column, packed column or column with rotating inserts. It is advantageous to use tray columns which can be operated continuously at a rate of from 0.1 to 0.4 part by volume/hour of ester entering the column per part by volume of the total capacity of the column. In the case of bubble-cap tray columns, a weir height of from 10 to 300 mm is preferred, whilst in the case of ball valve tray columns and sieve tray columns hole diameters of from 5 to 15 mm, ball diameters of from 8 to 30 mm and tray spacings of from 300 to 800 mm are preferred. In continuous operation, the steam can be introduced into the distillation boiler or, advantageously, between the lowest and next-but-lowest tray of the column. The ester I may be introduced together with the catalyst or separately therefrom; the separate feed points can be anywhere in the upper part of the column, but are preferably at the column top. It is advantageous to use a type of column which is insensitive to the low vapor throughput resulting from the face that the steam is introduced in virtually stoichiometric amount. Furthermore, it should be possible to select the residence time very precisely. This in itself is a reason for particularly preferring a bubble-cap tray column.

The hydrolysis may be carried out as follows: a mixture of the catalyst and the ester I is passed downward, and steam is passed upward, through a column, in the above amounts, and the hydrolysis is carried out in counter-current, at the reaction temperature. At the same time, the carboxylic acid formed is continuously removed as distillate and the α-naphthol is continuously removed from the bottom.

The α-naphthol obtainable by the process of the invention is a valuable starting material for the manufacture of dyes, drugs and insecticides, e.g. α-naphthyl N-methylcarbamate. It may also be used as a coupling component for azo dyes, as a starting material for indigoid dyes, and for the synthesis of 4-chloro-1-naphthol, 1-naphthol-2-carboxylic acid and naphthyl salicylate. Regarding the uses of the material, reference may be made to Ullmanns Encyklopädie der technischen Chemie, volume 12, pages 603–604.

In the Examples which follow, parts are by weight.

EXAMPLE 1

Per hour, 4,000 parts of naphthyl acetate and 40 parts of a 1:1 mixture of 4,8- and 2,6-dibutylnaphthalene-1-sulfonic acid are introduced, in the form of a melt, at 140° C., at the top end (above the top tray) of a bubble-cap tray column with 18 trays, operated at 140° C. At the bottom end (below the bottom tray), 390 parts of water per hour are introduced in the form of superheated steam at 150° C. under 1.3 bars. The residence time is 35 minutes. At the top of the column is a condenser, from which 1,270 parts per hour of acetic acid (99.9 percent by weight) are taken off. 2,095.6 parts/hour of naphthol, of boiling point 130° C./13 mbar, are taken off the bottom of the column. The yield is 96.8% of theory.

EXAMPLE 2 (COMPARATIVE EXAMPLE)

201 parts of α-naphthyl acetate and 45 parts of water are introduced into a stirred autoclave, the mixture is heated to 200° C., whilst stirring, resulting in an autogenous pressure of 15 bars. After 75 minutes at 200° C., the emulsion formed changes to a clear solution. After 6 hours at 200° C., the mixture is distilled. 134.5 parts of α-naphthol (86.5% of theory) of boiling point 130° C./13 mbar, 3 parts of naphthyl acetate and 9.5 parts of residue are obtained.

We claim:

1. A process for the manufacture of α-naphthol by hydrolyzing a carboxylic acid ester with steam in a distillation column in the presence of an acid, wherein an α-naphthyl ester of an aliphatic carboxylic acid, of the formula

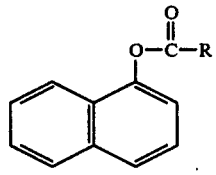

I, where R is hydrogen or alkyl group of 1 to 7 carbon atoms, said alkyl group substituted by alkyl or alkoxy each of 1 to 4 carbon atoms, and an organic sulfonic acid selected from the group consisting of a monoalkanesulfonic acid of 1 to 6 carbon atoms, an alkanedisulfonic acid of 1 to 6 carbon atoms, a haloalkanesulfonic acid or a monoalkanesulfonic acid respective of 1 to 6 carbon atoms, a perfluorinated alkanesulfonic acid of 1 to 6 carbon atoms, a benzenesulfonic acid, a partially hydrogenated aromatic sulfonic acid, a carboxybenzenesulfonic acid, a halobenzenesulfonic acid, a hydroxybenzenesulfonic acid or a polynuclear aromatic sulfonic acid, are passed downwardly through the column while steam is passed upwardly therein counter-current flow, and the reaction is carried out at from 100° to 170° C. using from 0.9 to 1.5 moles of water per mol of said α-naphthyl ester.

2. A process as claimed in claim 1, wherein the reaction is carried out at from 120° to 155° C.

3. A process as claimed in claim 1, wherein the reaction is carried out at from 130° to 145° C.

4. A process as claimed in claim 1, wherein the ester I is brought to a temperature of from 120° to 180° C. before it enters the column.

5. A process as claimed in claim 1, wherein the reaction is carried out with a residence time of from 10 to 90 minutes.

6. A process as claimed in claim 1, wherein the reaction is carried out with from 0.9 to 1.1 moles of water, in the form of steam, per mole of α-naphthyl ester I.

7. A process as claimed in claim 1, wherein the reaction is carried out with from 0.95 to 1.05 moles of water, in the form of steam, per mole of α-naphthyl ester.

8. A process as claimed in claim 1, wherein the reaction is carried out using steam supplied at from 100° to 170° C.

9. A process as claimed in claim 1, wherein the reaction is carried out under a pressure of from 1 to 3 bars.

10. A process as claimed in claim 1, wherein the reaction is carried out using from 0.002 to 0.02 mole of sulfonic acid per mole of starting material I.

11. A process as claimed in claim 1, wherein the reaction is carried out using an organic sulfonic acid selected from the group consisting of methanesulfonic acid, ethanesulfonic acid, propane-1-sulfonic acid, n-butane-1-sulfonic acid, n-pentane-1-sulfonic acid, n-hexane-1-sulfonic acid, methanedisulfonic acid, ethane-1,2-disulfonic acid, 2-chloroethane-1-sulfonic acid, 2-hydroxyethane-1-sulfonic acid, 3-hydroxypropane-1-sulfonic acid, 3-hydroxybutane-1-sulfonic acid, 4-hydroxybutane-1-sulfonic acid, 1-chlorobutane-3-sulfonic acid and 1-chlorobutane-4-sulfonic acid, perfluoromethanesulfonic acid, perfluoroethanesulfonic acid, perfluoropropane-1-sulfonic acid, perfluorobutane-1-sulfonic acid, perfluoropentane-1-acid, and perfluorohexane-1-sulfonic acid, benzenemonosulfonic acid, benzene-1,2-disulfonic acid, benzene-1,3-disulfonic acid, benzene-1,4disulfonic acid, 2-methylbenzenesulfonic acid, 3-methylbenzenesulfonic acid, 4-methylbenzenesulfonic acid, 2,4-dimethylbenzenesulfonic acid, 2,5-dimethylbenzenesulfonic acid, 2,4,5-trimethylbenzenesulfonic acid, 4-isopropylbenzenesulfonic acid, 4-n-oxtylbenzenesulfonic acid, 2-, 3- or 4-dodecylbenzenesulfonic acid, indane-5-sulfonic acid, tetralin-2-sulfonic acid, 2-carboxybenzenesulfonic acid, 3-carboxybenzenesulfonic acid, 4-carboxybenzenesulfonic acid, 3,5-dicarboxybenzenesulfonic acid, 3,4-dicarboxybenzenesulfonic acid, 2-chloro-5-carboxybenzenesulfonic acid, 3-chloro-4-carboxybenzenesulfonic acid, 4-chlorobenzenesulfonic acid, 3-chlorobenzenesulfonic acid, 2-chlorobenzenesulfonic acid, 2,5 dichlorobenzenesulfonic acid, 3,4-dichlorobenzenesulfonic acid, 2,4,5-trichlorobenzenesulfonic acid, 2-hydroxybenzenesulfonic acid, 3-hydroxybenzenesulfonic acid, 4-hydroxybenzenesulfonic acid, 3-chloro-4- methylbenzenesulfonic acid, 5-chloro-2-methylbenzenesulfonic acid, 4-chloro-3-methylbenzenesulfonic acid, 3-chloro-4-hydroxybenzenesulfonic acid, 5-chloro-2-hydroxybenzenesulfonic acid, benzophenone-4-sulfonic acid, diphenylmethane-4-sulfonic acid, diphenylsulfone-3-sulfonic acid, naphthalene-1-sulfonic acid, naphthalene-2-sulfonic acid, naphthalene-1-5-disulfonic acid, naphthalene-1,6-disulfonic acid, naphthalene-2,6-disulfonic acid, naphthalene-2,7-disulfonic acid, naphthalene-1,3,6-trisulfonic acid, diphenylether-4-sulfonic acid, acenaphthalene-3-sulfonic acid, acenaphthalene-5-sulfonic acid, 2,3-dibutyl-naphthalene-1-sulfonic acid, 2,4-dibutyl-naphthalene-1-sulfonic acid, 2,5-dibutyl-naphthalene-1-sulfonic acid, 2,6-dibutyl-naphthalene-b 1-sulfonic acid, 2,7-dibutyl-naphthalene-1-sulfonic acid, 2,8-dibutyl-naphthalene-1-sulfonic, 1,3-dibutyl-naphthalene-2-sulfonic acid, 1,4-dibutyl-naphthalene-2-sulfonic acid, 1,5-dibutyl-naphthalene-2-sulfonic acid, 1,6-dibutyl-naphthalene-2-sulfonic acid, 1,7-dibutyl-naphthalene-2-sulfonic acid, 1,8-dibutyl-naphthalene-2-sulfonic acid, homologous dimethyl, diethyl, di-n-propyl, diisopropyl, diisobutyl, di-sec., butyl and di-tert.-butyl derivatives of naphthalene-1-sulfonic acid and naphthalene-2-sulfonic acid.

* * * * *

UNITED STATES PATENT AND TRADEMARK OFFICE
CERTIFICATE OF CORRECTION

PATENT NO. : 4,171,459

DATED : October 16, 1979

INVENTOR(S) : SCHUSTER ET AL

It is certified that error appears in the above—identified patent and that said Letters Patent is hereby corrected as shown below:

Column 6, line 48, change "perfluoropentane-1-acid" to--perfluoropentane-1-sulfonic acid--

Column 6, line 51, should be "benzene-1,4- disulfonic" (the dash after "4" is missing)

Column 8, line 1, "b" at end of line should not be shown

Signed and Sealed this

*Twenty-second* Day of *April 1980*

[SEAL]

*Attest:*

SIDNEY A. DIAMOND

*Attesting Officer*   *Commissioner of Patents and Trademarks*